(12) United States Patent
Axén et al.

(10) Patent No.: US 8,556,495 B2
(45) Date of Patent: Oct. 15, 2013

(54) INJECTOR DEVICE (75) Inventors: Niklas Axén, Järlåsa (SE); Hans Lennernäs, Uppsala (SE); Johan Yngve, Mjölby (SE); Lars Åke Malmsten, Lund (SE); Gunilla Eketorp, Danderyd (SE); Åke G. Pilbrant, Kungsbacka (SE)

(73) Assignee: Lidds AB, Helsingborg (SE)

( * ) Notice: Subject to any disclaimer, the term of this patent is extended or adjusted under 35 U.S.C. 154(b) by 108 days.

(21) Appl. No.: 13/119,258

(22) PCT Filed: Sep. 22, 2009

(86) PCT No.: PCT/EP2009/006835
§ 371 (c)(1),
(2), (4) Date: May 9, 2011

(87) PCT Pub. No.: WO2010/034462
PCT Pub. Date: Apr. 1, 2010

(65) Prior Publication Data
US 2011/0222366 A1 Sep. 15, 2011

(30) Foreign Application Priority Data
Sep. 29, 2008 (DK) .................................. 2008 01355

(51) Int. Cl.
*B01F 15/02* (2006.01)
(52) U.S. Cl.
USPC .......................................................... 366/189
(58) Field of Classification Search
USPC .......... 366/194–196, 241, 332, 333, 189, 184
See application file for complete search history.

(56) References Cited

U.S. PATENT DOCUMENTS

| 3,195,778 A | 7/1965 | Coates |
| 4,011,868 A | 3/1977 | Friend |

(Continued)

FOREIGN PATENT DOCUMENTS

| EP | 1 433 446 A2 | 6/2004 |
| EP | 1 913 888 A2 | 4/2008 |
| JP | 2005-323849 A | 11/2005 |
| SE | 2004/0353 | 11/2004 |
| WO | WO 2005/048886 A2 | 6/2005 |

OTHER PUBLICATIONS

International Search Report (PCT/ISA/210) issued on Nov. 16, 2009, by European Patent Office as the International Searching Authority for International Application No. PCT/EP2009/006835.

(Continued)

*Primary Examiner* — Tony G Soohoo
*Assistant Examiner* — Anshu Bhatia
(74) *Attorney, Agent, or Firm* — Buchanan Ingersoll & Rooney PC (57) ABSTRACT An injector device is disclosed, the injector device comprising an elongated mixing container extending along a first axis, and a piston member slidably positioned in the mixing container. The injector device comprises a mixing device comprising a mixing member, an elongated member parallel to the first axis and a handle member. The piston member comprises a piston head and a first locking arm flexibly connected to the piston head, such that the first locking arm in a first position extends substantially parallel to the elongated member and engages with the mixing device in such a way that the piston member moves in a first direction along the first axis with the mixing device. In a second position, the first locking arm may allow the mixing device to move relative to the mixing container independently of the piston member.

20 Claims, 7 Drawing Sheets

(56) References Cited

U.S. PATENT DOCUMENTS

| | | | |
|---|---|---|---|
| 4,340,056 A | | 7/1982 | Erb |
| 4,465,476 A | | 8/1984 | Gähwiler |
| 4,767,413 A | * | 8/1988 | Haber et al. ............ 604/198 |
| 5,143,211 A | * | 9/1992 | Miczka et al. ........... 206/221 |
| 5,688,250 A | * | 11/1997 | Naganuma ............ 604/200 |
| 6,488,651 B1 | | 12/2002 | Morris et al. |
| 6,550,957 B2 | | 4/2003 | Mizutani et al. |
| 7,018,089 B2 | | 3/2006 | Wenz et al. |
| 2002/0035350 A1 | * | 3/2002 | Turnbull et al. ........ 604/110 |
| 2003/0012079 A1 | | 1/2003 | Coffeen et al. |

OTHER PUBLICATIONS

Written Opinion (PCT/ISA/237) issued on Nov. 16, 2009, by European Patent Office as the International Searching Authority for International Application No. PCT/EP2009/006835.

International Preliminary Report on Patentability (PCTIPEA/409) issued on Jan. 14, 2011, by European Patent Office as the International Searching Authority for International Application No. PCT/EP2009/006835.

* cited by examiner

INJECTOR DEVICE

The present invention relates to an injector device, in particular an injector device adapted for mixing components for preparation of a composition to be injected through a cannula into the body of a subject.

At medical or surgical treatment of living beings, there is often a need to inject a composition of at least two components into the body of a subject. In some applications, a first component and a second component, typically a powder and a liquid are mixed shortly or just before the injection. It is important that the resulting composition is a homogeneous composition. Furthermore, it may be important that the composition itself or one or more of the components are sterile.

Typically, the mixing of the components is performed outside a syringe, subsequently drawn into the syringe barrel and then injected into the body.

There is a need for an injector device that enables thorough mixing of a first component and a second component in a sterile environment. Mixing of powder and liquid to a paste is more difficult and requires more energy than dissolving a powder in a liquid.

Further it is an object to provide an injector device that is simple to use and operate. Typically, such devices are single use, and accordingly it is an object to provide a cheap injector device.

Accordingly, an injector device is provided, the injector device comprising an elongated mixing container extending along a first axis, and a piston member slidably positioned in the mixing container. The injector device further comprises a mixing device comprising a mixing member, an elongated member parallel to the first axis and a handle member. The piston member comprises a piston head and a first locking arm flexibly connected to the piston head, such that the first locking arm in a first position extends substantially parallel to the elongated member and engages with the mixing device in such a way that the piston member moves in a first direction along the first axis with the mixing device. In a second position, the first locking arm may allow the mixing device to move relative to the mixing container independently of the piston member.

Further disclosed is a method for mixing a first component and a second component using an injector device comprising an elongated mixing container extending along a first axis, and a piston member slidably positioned in the mixing container, wherein the injector device further comprises a mixing device comprising a mixing member, an elongated member parallel to the first axis and a handle member, the piston member comprising a piston head and a first locking arm flexibly connected to the piston head. The method comprises providing a first and a second component in the mixing container, bending the first locking arm into a second position, wherein the mixing device is allowed to move relative to the mixing container independently of the piston member, mixing the first and second component by moving the mixing device along the first axis, moving the first locking arm into a first position, wherein the first locking arm extends substantially parallel to the elongated member and engages with the mixing device in such a way that the piston member is moved in a first direction along the first axis with the mixing device, and moving the mixing device in the first direction.

It is an important advantage of the present invention that the mixing of two components can be performed in the mixing container and that the composition can be injected directly from the mixing container without the need for transferring the composition to another container before injection.

A further advantage lies in that the injector device may be prefilled, e.g. with a first component such as a powder, beads, e.g. beads comprising one or more layers of coating, and thus function as a storage container.

It is an advantage of the present invention that the injector device comprises few components making it simple and cheap to produce.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

The figures are schematic and simplified for clarity, and they merely show details which are essential to the understanding of the invention, while other details have been left out. Throughout, the same reference numerals are used for identical or corresponding parts.

It should be noted that in addition to the exemplary embodiments of the invention shown in the accompanying drawings, the invention may be embodied in different forms and should not be construed as limited to the embodiments set forth herein. Rather, these embodiments are provided so that this disclosure will be thorough and complete, and will fully convey the concept of the invention to those skilled in the art.

The injector device according to the present invention comprises an elongated mixing container. The mixing container, preferably tubular and having a circular cross-section perpendicular to and along the first axis, has a first end and an open second end. Preferably, a coupling element, e.g. including a cap or plug, is provided at the first end, e.g. in order to facilitate coupling or attachment of a needle, cannula, tubing, syringe or the like to the injector device. An opening may be provided at the first end to allow introduction of one or more components, e.g. a liquid to be mixed with powder in the mixing container.

The mixing container may comprise one or more protrusions extending radially at the open second end of the mixing container, e.g. a first flange part and/or a second flange part perpendicular to the first axis. These protrusions may function as supports during injection or guide the one or more locking arms, e.g. in the second position, during mixing and/or contribute to increase stability of the mixing container.

The injector device comprises a piston member slidably positioned in the mixing container. The piston member comprises a piston head and one or more locking arms including a first locking arm.

The piston member may comprise a second locking arm flexibly connected to the piston head. The second locking arm may be arranged such that the second locking arm in a first position extends substantially parallel to the elongated member and engages with the mixing device in such a way that the piston head moves with the mixing member in the first direction, and in a second position allows the mixing device to move relative to the mixing container independently of the piston member. The piston member may comprise a third locking arm flexibly connected to the piston head. The third locking arm may be arranged such that the third locking arm in a first position extends substantially parallel to the elongated member and engages with the mixing device in such a way that the piston head moves with the mixing member in the first direction, and in a second position allows the mixing device to move relative to the mixing container independently of the piston member.

For a piston member comprising a plurality of locking arms, the connection points of the locking arms may be equidistantly distributed along the circumference of the piston head, e.g. 180° for a two-arm piston member, 120° for a three-arm piston member. However, other configurations may be employed.

The locking arm(s) enables injection of composition in the first position and mixing of composition in the second position. In the first position, the piston member and the mixing device constitute a piston assembly for injection of composition. In the second position, the locking arms may enable a user to lock the piston member in relation to the mixing container and allow the user to move the mixing device in relation to the mixing container and the piston member.

An important advantage of the present invention resides in that the locking arm(s) in the first position together with the elongated member provide a substantially rigid and stable piston rod, i.e. the locking arm(s) and the elongated member constitute a piston rod or at least a part of a piston rod in order to facilitate emptying of the mixing container.

The first and/or second locking arm each has a proximal end flexibly connected to the piston head and a distal end. The distal end of the locking arm(s) may be formed to, in the first position, engage with or support on the handle member. In an embodiment, the distal end may be formed to, in the first position, engage with or support on the elongated member, e.g. engage in a recess in the elongated member.

The locking arm(s) are flexibly connected to the piston head, i.e. the locking arms can be moved or bent in relation to the piston head, for example by bending or by a pivoting. The proximal end of the locking arms may be flexibly connected to the piston head via a hinge part, respectively, enabling the locking arms to pivot, e.g. about a bending axis perpendicular to the first axis, between the first position and the second position. Preferably, a part or portion of the piston member between the piston head and the first locking arm forms a first hinge part, and a part of the piston member between the piston head and the second locking arm forms a second hinge part. Preferably, the hinge parts have suitable thickness and length to form part of a substantially rigid piston rod when the locking arm(s) is/are in the first position and at the same time enabling a user to pivot or bend the locking arm(s) to the second position enabling movement of the mixing device along the first axis independently of the piston member.

The locking arm(s) may be adapted to in the second position support on the outer surface of the mixing container. Accordingly, the piston member may comprise one or more support elements extending from the locking arm(s). In the second position, the locking arm(s) may extend parallel to the first axis with the distal end(s) pointing in the first direction. Thereby, a user may be able to have a firm grip on the injector device during mixing, which may be advantageous in cases where properties of the composition may render mixing difficult.

In an embodiment, a support element is arranged near or at the distal end of each of the locking arm(s). The support element may have a concave edge shape adapted to support on the outer surface of the mixing container.

In the first position, the locking arm(s), e.g. the first and/or the second locking arm, may be arranged to lock the mixing device in relation to the piston member when the mixing device and the piston member are moved both in the first direction and in a second direction opposite the first direction along the first axis.

In the first position of the locking arm(s), the piston member may move along the first axis in relation to the mixing container.

In the second position, the locking arm(s), e.g. the first and/or the second locking arm, may be arranged such that the piston member is prevented from moving in the first direction in relation to the mixing container. In the second position, the first and/or the second locking arm may be substantially parallel to the first axis.

In the second position, the locking arm(s), e.g. the first and/or the second locking arm, may extend parallel or substantially parallel to the first axis with the distal end(s) pointing in the first direction corresponding to an angle of 0° between the locking arm(s) and the first axis.

In the second position, the locking arm(s), e.g. the first and/or the second locking arm, may be bent such that the respective locking arm forms an angle in the range from 0° to 90° with the first axis in the first direction, where an angle of 0° corresponds to the distal ends of the locking arms pointing in the first direction. The angle may be in the range from 0° to 60° such as in the range from 0° to 45°, in the range from 0° to 30°, e.g. in the range from 0° to 15°. An angle in the range from 0° to 90° may be preferred since such angle facilitates movement of the mixing device. An angle larger than 90°, e.g. up to 135°, may be employed.

The locking arm(s), e.g. the first and/or the second locking arm, may during injection and/or in the first position be positioned between the elongated member of the mixing device and the mixing container seen radially from the first axis. Further, the locking arm(s), e.g. the first and/or the second locking arm, may during mixing and/or in the second position be positioned such that the locking arm(s) extends along the outside of the mixing container.

The first and/or second locking arms may have any suitable length depending on the length of the mixing container. For example, the first and/or second locking arms may have a length in the range from about 1 cm to about 30 cm, such as in the range from about 3 cm to about 10 cm, e.g. about 6 cm.

The piston member may comprise one or more piston elements assembled to form the piston member. In an embodiment, the piston member comprises a first piston element forming the locking arm(s) and a part of the piston head. Further, the piston member may comprise a second and/or a third piston element forming part(s) of the piston head. The piston elements may be assembled by gluing, mechanical press fit, welding or a combination.

In an embodiment of the present invention, the piston member or parts thereof is an integrated part e.g. produced by injection molding techniques, over-molding techniques, a combination or others.

The piston head may have a bore. Preferably, the bore is a cylindrical, central bore parallel to the first axis. Further, the bore may be adapted to slidably accommodate the elongated member of the mixing device. Preferably, the bore has a circular cross-section perpendicular to the first axis to allow rotation of the mixing device around the first axis for improved mixing, however a non-circular cross-section, such as oval, polygonal or other may be employed.

A tight seal may be formed between the bore wall and the elongated member of the mixing device. The piston member may comprise one or more inner seal rings, e.g. a first and a second inner seal ring. The one or more inner seal rings may be at least partly accommodated in one or more recesses formed in the bore surface. In an embodiment, one or more inner seal rings are molded or glued onto the bore surface. A plurality of inner seal rings is preferred in order to improve stability of the injector device.

In a preferred embodiment, the one or more inner seal rings comprises a first inner O-ring accommodated in an annular first inner recess in the bore surface and a second inner O-ring accommodated in an annular second inner recess in the bore surface.

A tight seal may be formed between the piston member and the inner wall of the mixing container. The piston member may comprise one or more outer seal rings, e.g. a first and a second outer seal ring. The one or more outer seal rings may be at least partly accommodated in one or more recesses formed in the surface of the piston head. In an embodiment, one or more outer seal rings are molded or glued onto the piston head surface. A plurality of outer seal rings is preferred in order to improve stability of the injector device.

In a preferred embodiment, the one or more outer seal rings comprises a first outer O-ring accommodated in an annular first outer recess and a second outer O-ring accommodated in an annular second outer recess.

The injector device comprises a mixing device comprising a mixing member, an elongated member parallel to the first axis and a handle member. The mixing member may have any suitable shape and be formed in order to facilitate a thorough mixing of components in the mixing container. The elongated member may comprise a rod. The rod may be a hollow rod. Preferably, the elongated member has a circular cross-section perpendicular to the first axis to allow rotation of the mixing device around the first axis independent of the piston member for improved mixing, however a non-circular cross-section, such as oval, polygonal or other may be employed if and when rotation of the piston member in relation to the mixing device is not desired.

The handle member may provide for a user to grip, move and rotate the mixing device. The handle member may be adapted to form a support for the first and/or the second locking arm in the first position of the locking arm(s). In an embodiment, the handle member may be adapted to engage with the locking arm(s) such that the locking arms are kept locked parallel to the first axis.

The mixing member may have any suitable shape and be formed in order to facilitate a thorough mixing of components in the mixing container. In an embodiment, the mixing member forms one or more mixing wings, e.g. two, three, or more mixing wings. The mixing wings may have one or more openings, e.g. one, two, three or more openings. The openings may have any suitable shape. For example, the openings may have a circular, polygonal, or oval cross section. In an embodiment, the openings may have a size in the range from about 1 $mm^2$ to about 30 $mm^2$, e.g. about 3 $mm^2$. Preferably, the mixing member is shaped to fit with the inside of first end of the mixing container to provide best possible emptying of the injector device, i.e. reduce the amount of discarded composition.

Preferably, the mixing member with mixing wings and openings is formed to facilitate mixing of the composition, e.g. by creating a high degree of turbulence in the composition, when the mixing member is moved along the first axis and/or when the mixing member is rotated around the first axis.

The mixing member, the elongated member and the handle member may be assembled by gluing, mechanical press fit, welding or a combination. In an embodiment, the mixing member and the elongated member are injection moulded in the same mould and thus form one blank or part. In an embodiment, the handle member and the elongated member are injection moulded in the same mould and thus form one blank or part.

Preferably, the injector device or different parts of the injector device, such as the mixing device, the piston member, and/or the mixing container, are made of a plastic material suitable for injection moulding. The plastic material may be polyethylene (PE), high-density polyethylene (HDPE), polypropylene (PP), polystyrene, or other polyolephines, or a combination thereof.

It is an important advantage of the present invention that the injector device can be sterilized with radiation, such as gamma radiation, alpha radiation and/or beta radiation.

Further, it is an advantage that mixing and/or injection with the injector device can be performed without removing the mixing member or parts thereof from the injector device which simplifies operation and use.

The method for mixing a first component and a second component may be performed using an injector device as disclosed herein. The injector device may be connected to a syringe and the method may comprise pumping, with the locking arm(s) in the first position, at least a part of the composition comprising the first component and the second component from the injector device into the syringe, e.g. back and forth between the injector device and the syringe.

Pumping the composition back and forth may enhance mixing by flushing the coupling element, thereby removing any dry powder that may be left there in the opening.

Figure 1:
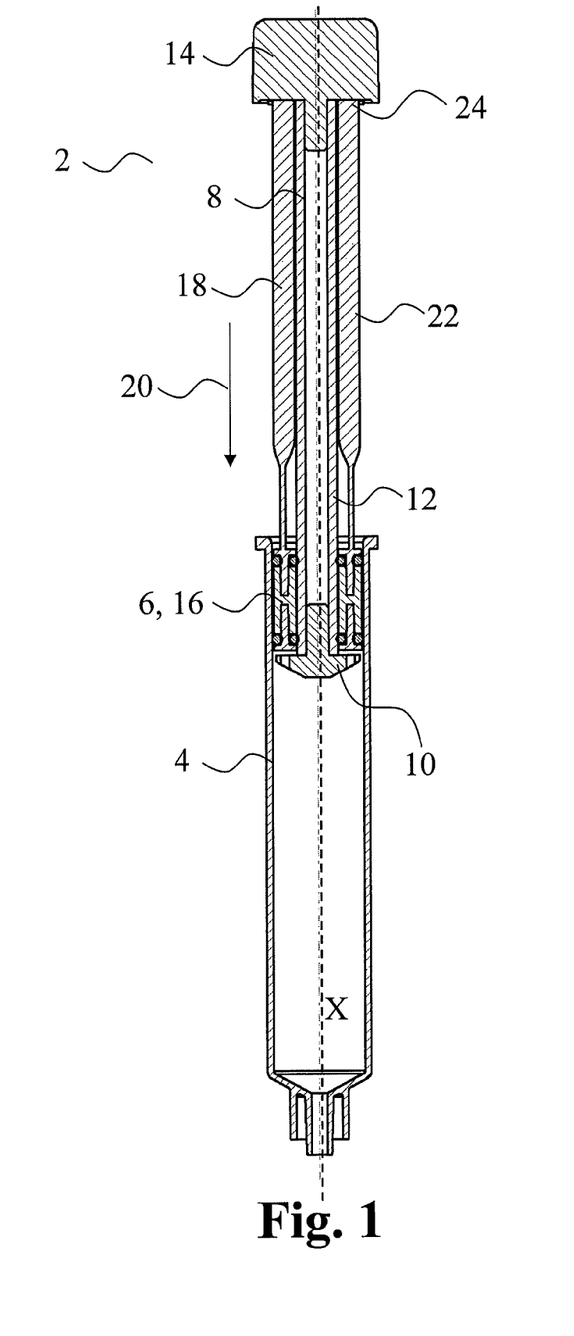
FIG. 1 is a cross-section of an embodiment of an injector device according to the invention with locking arms in a first position.

FIG. 1 shows a cross-section of an embodiment of the injector device according to the invention. The injector device 2 comprises an elongated mixing container 4 extending along a first axis X, and a piston member 6 slidably positioned in the mixing container 4. Further, the injector device 2 comprises a mixing device 8 comprising a mixing member 10, an elongated member 12 parallel to the first axis X and a handle member 14. The piston member 6 comprises a piston head 16 and a first locking arm 18 and a second locking arm 22 flexibly connected to the piston head 16. A first locking arm 18 may be sufficient; however a first locking arm 18 and a second locking arm 22 are preferred for stability during injection.

In a first position or injecting position as illustrated in FIG. 1, the first locking arm 18 and the second locking arm 22 extend substantially parallel to the elongated member 12 and engages with the mixing device 8 in such a way that the piston member 6 is adapted to move with the mixing device 8 in a first direction (indicated by arrow 20) along the first axis. When a user pushes the mixing device 8 into the mixing container 4, the piston member is also pushed into the mixing container due to the locking arms 18, 22 supporting on or engaging with the mixing device 8. In the illustrated injector device 2, the distal ends 24 of the locking arms 18, 22 support on the handle member 14. The first locking arm 18 and the second locking arm 22 have a length of about 6 cm.

Figure 2:
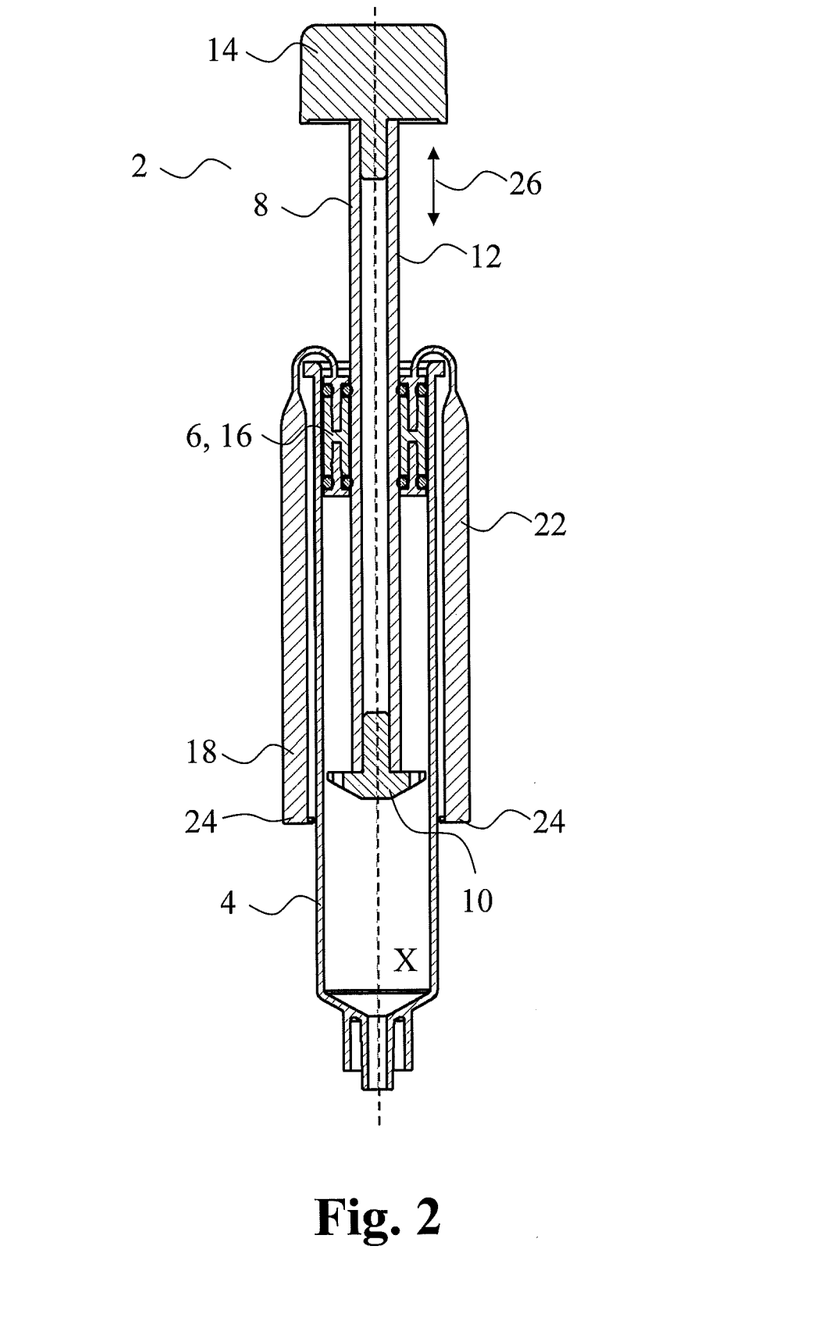
FIG. 2 is a cross-section of the embodiment of FIG. 1 with locking arms in a second position.

FIG. 2 illustrates the injector device 2 having the locking arms 18, 22 in a second position or a mixing position. The locking arms 18, 22 have been folded over the mixing container wall such that the locking arms 18, 22 are substantially parallel to the first axis X and the distal ends 24 pointing in the first direction indicated by arrow 20. Thereby, the mixing device can move in relation to the piston member 6 and the mixing container 4 along the first axis X, allowing a user to mix a composition in the mixing container 4 (indicated by double arrow 26). The circular cross-section of the elongated member 12 enables a user to rotate the mixing device around the first axis independently of the piston member and the mixing container. Thereby, an improved mixing may be obtained. Further, the position of the locking arms ensures that the piston member 6 is prevented from moving in the first direction.

Figure 3:
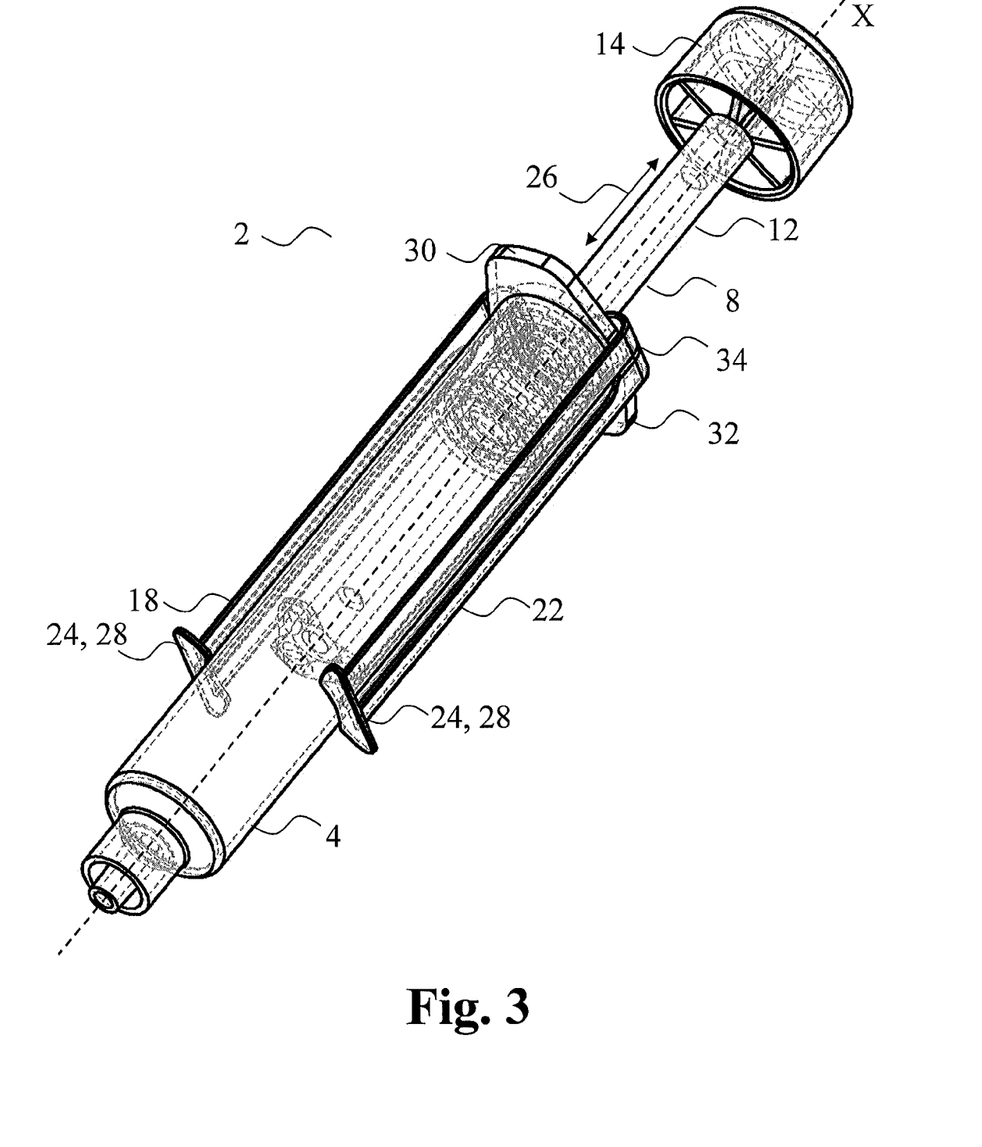
FIG. 3 is a perspective view of the embodiment of FIG. 1.

FIG. 3 shows a perspective view of the injector device 2. The locking arms 18, 22 are in the second position. A first support element 28 is provided at the distal ends 24 of the first and second locking arms 18, 22. The first support element 28 supports on the outer surface of the mixing container. The first support element 28 has a concave edge shape adapted to support on the outer surface of the mixing container enabling a user to obtain an improved grip during mixing. Further, the first support element 28 is adapted to support onto the handle member 4, when the locking arms 18, 22 are in the first position. In an embodiment, the first support element(s) 28 may be adapted to engage with the elongated member 12 in the first position, e.g. by provision of one or more recesses in the surface of the elongated member 12.

The mixing container 4 comprises a first flange part 30 and a second flange part 32 perpendicular to the first axis X at the open second end 34 of the mixing container 4.

Figure 4:
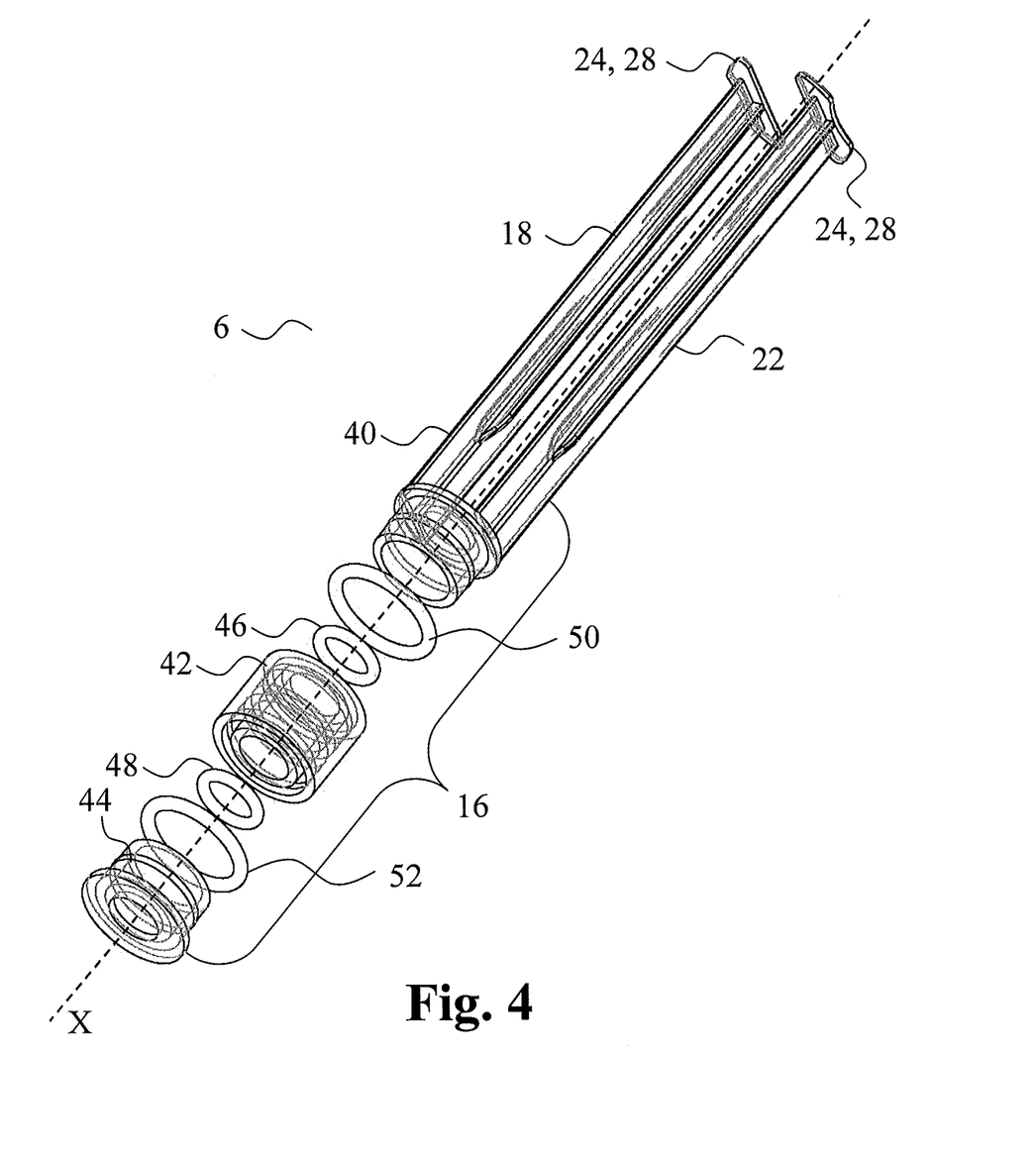
FIG. 4 is an exploded view of an exemplary piston member of the injector device according to the present invention.

FIG. 4 is an exploded view of the piston member 6. The piston member 6 comprises piston elements assembled to form the piston member. A first piston element 40 forms the locking arm(s) 18, 22 and a part of the piston head 16. Further, the piston member 6 comprises a second 42 and a third 44 piston element forming parts of the piston head 16. In the illustrated embodiment, the piston elements are assembled by mechanical press fit. Furthermore, the piston member comprises a first inner seal ring 46, a second inner seal ring 48, a first outer seal ring 50, and a second outer seal ring 52. When the piston elements 40, 42, 44 are assembled, a central bore parallel to the first axis X is formed in the piston head 16. Annular first and second inner recesses are formed in the bore surface to accommodate the first inner seal ring 46 and the second inner seal ring 48, respectively. Further, annular first and second outer recesses are formed in the piston head surface to accommodate the first outer seal ring 50 and the second outer seal ring 52, respectively.

Figure 5:
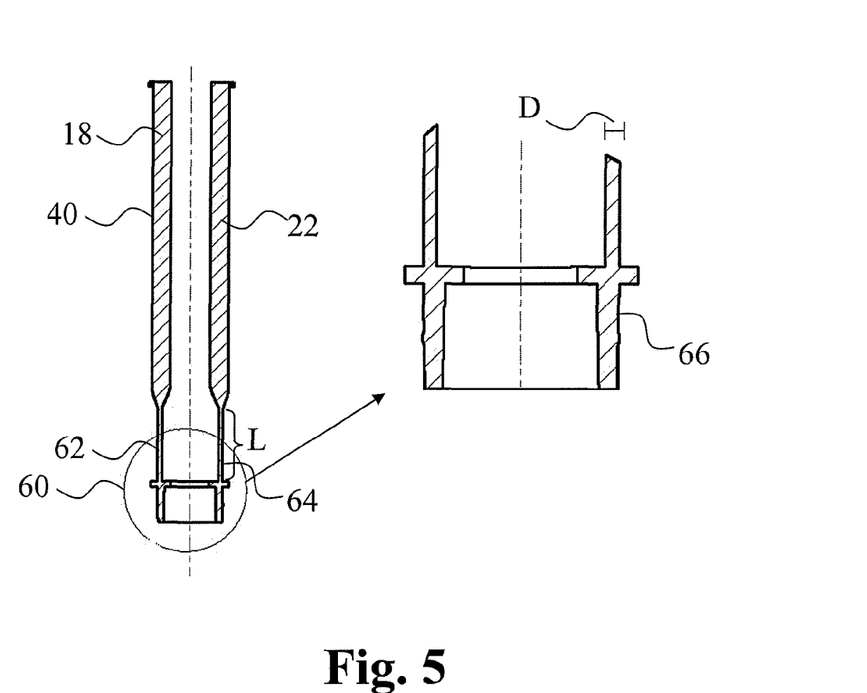
FIG. 5 is a cross-section of a first piston element of the piston member of FIG. 4.

FIG. 5 is a cross-section of the first piston element 40. The first piston element 40 comprises the first locking arm 18 and second locking arm 22. Each locking arm 18, 22 is flexibly connected to a first piston member element 60 via first and second hinge parts 62, 64, respectively. The hinge parts 62, 64 are formed as bending zones having suitable flexibility to allow pivoting of the locking arms with respect to the piston head 16. The first piston member element 60 has a central circular bore for the elongated member. A cylindrical wall 66 forms a coupling member for coupling the first piston element 40 to the second piston element 42. One or more, optionally annular, protrusions or recesses may be formed on the inner or outer surface of the cylindrical wall to provide a mechanical press fit between the first piston element 40 and the second piston element 42.

In general, the hinge parts are formed in such a way that the locking arms can be pivoted between desired positions about an axis substantially perpendicular to the first axis. Further, the hinge parts are formed in such a way as to provide a suitable rigidity in order to enable movement of the piston head in the first direction when a load is applied to the handle member and the locking arm(s) being in the first position. The bending zones may have any suitable thickness D and length L. For example, the bending zones may have a thickness D in the range from 0.1 mm to about 10 mm, preferably in the range from 0.5 mm to about 2 mm. In the embodiment illustrated in FIG. 5, D is about 0.7 mm. The length L may be in the range from about 1 mm to about 30 mm, e.g. in the range from about 5 mm to about 20 mm. In the embodiment illustrated in FIG. 5, L is about 13 mm.

Figure 6:
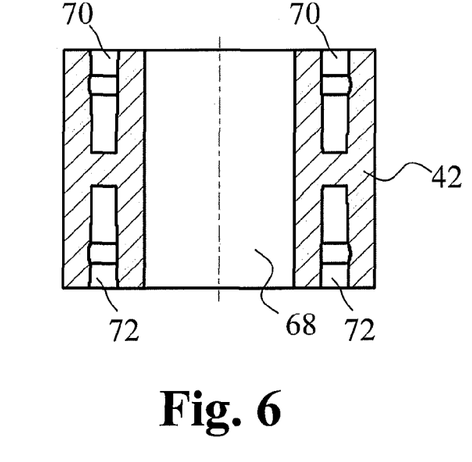
FIG. 6 is a cross-section of a second piston element of the piston member of FIG. 4.

FIG. 6 is a cross-section of the second piston element 42. The second piston element 42 is a substantially cylindrical member having a central, circular bore 68. At each end of the second piston element a coupling member 70, 72, respectively, is formed as an annular recess. The coupling member 70 is adapted for coupling the first piston element 40 and the second piston element 42.

Figure 7:
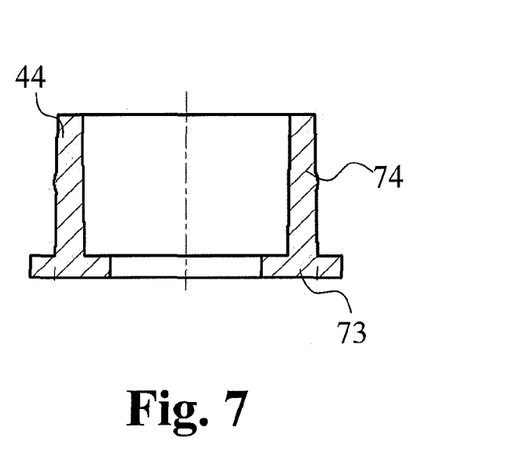
FIG. 7 is a cross-section of a third piston element of the piston member of FIG. 4.

FIG. 7 is a cross-section of the third piston element 44. The third piston element 44 has flange part 73 having a central circular bore for accommodation of the elongated member 12. A cylindrical wall 74 forms a coupling member for coupling the third piston element 44 to the second piston element 42. One or more, optionally annular, protrusions or recesses may be formed on the inner or outer surface of the cylindrical wall 74 to provide a mechanical press fit between the third piston element 44 and the second piston element 42.

Figure 8:
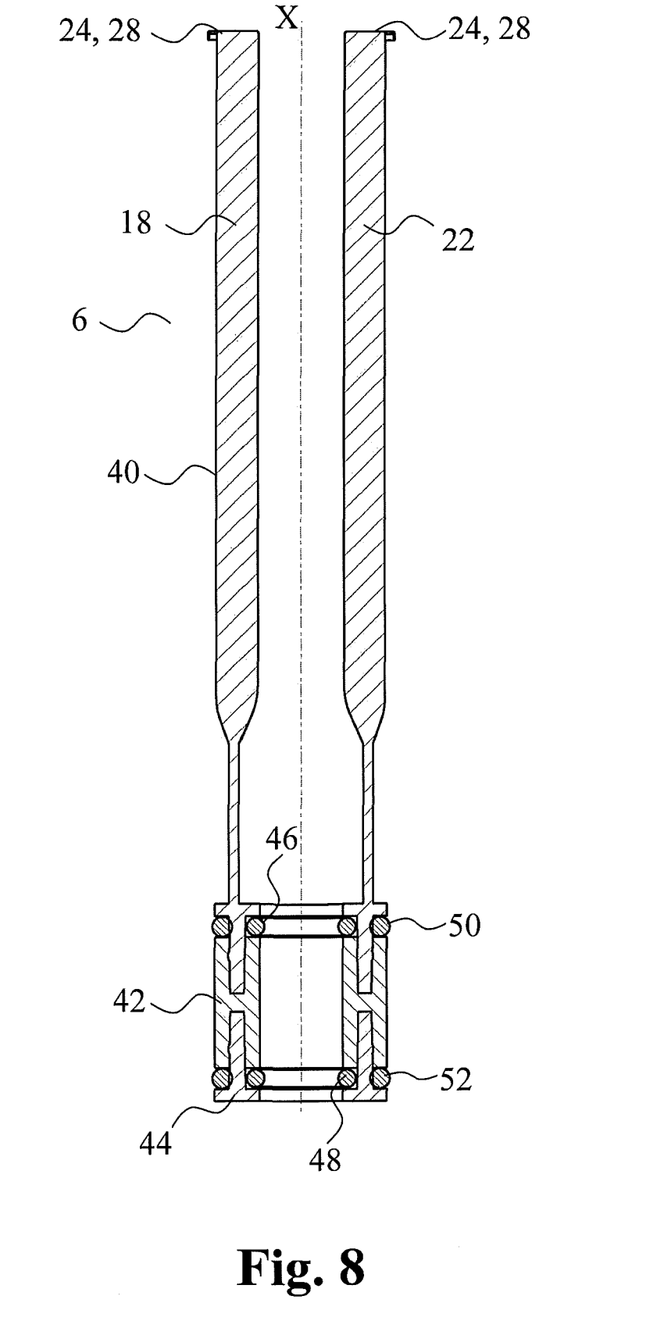
FIG. 8 is a cross-section of the assembled piston member of FIG. 4.

FIG. 8 is a cross-section of the assembled piston member. When assembled, the first 40, second 42, and third 44 piston elements form inner and outer annular recesses for accommodating inner 46, 48 and outer 50, 52 seal rings, respectively.

Figure 9:
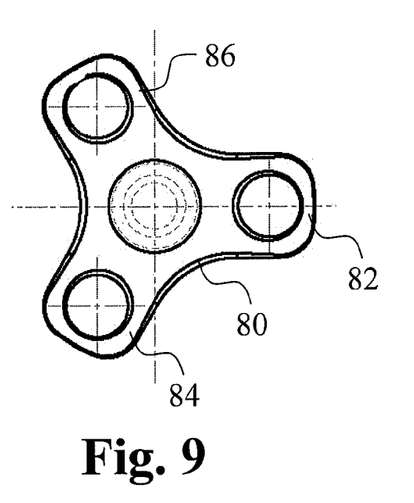
FIG. 9 is an end view of an exemplary mixing member of the mixing device.
Figure 10:
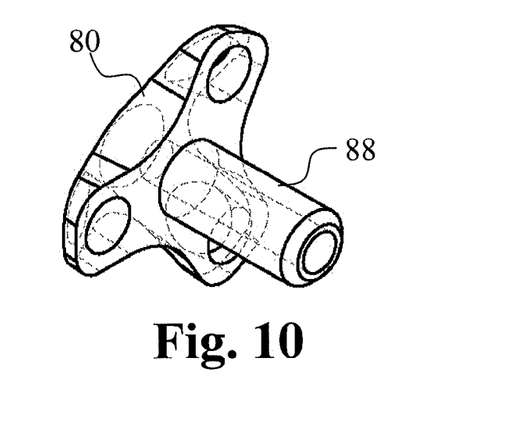
FIG. 10 is a perspective view of the mixing member of FIG. 9.

FIG. 9 is an end view and FIG. 10 is a perspective view of an exemplary mixing member 80 of the present invention. The mixing member 80 is formed in order to facilitate a thorough mixing of components in the mixing container. The mixing member comprises three mixing wings 82, 84, 86, each having at least one opening. The mixing member 80 is shaped to fit with the inside of first end of the mixing container to provide best possible emptying of the injector device, i.e. reduce the amount of discarded composition. The mixing member 80 comprises a coupling member 88 in the form of an, optionally hollow, rod for coupling to the elongated member 12.

Figure 11:
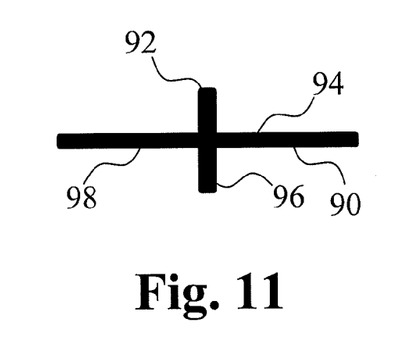
FIG. 11 is a cross-section of an exemplary locking arm.
Figure 12:
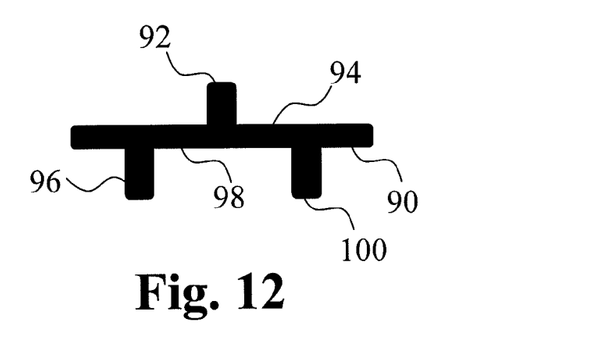
FIG. 12 is a cross-section of an exemplary locking arm.

FIGS. 11 and 12 show cross-sections of exemplary locking arms, e.g. the first locking arm 18 and/or the second locking arm 22. In FIG. 11, the locking arm has a flat base 90 with a first supporting protrusion 92 extending perpendicularly from the first side 94 and a second supporting protrusion 96 extending perpendicularly from the second side 98. In an embodiment of the present invention, the first side 94 of the locking arm faces the elongated member 12 in the first position. In another embodiment, the second side 98 of the locking arm faces the elongated member 12 in the first position. In FIG. 12, a third supporting protrusion 100 extends perpendicularly from the second side. The protrusions on each side may be directly opposite each other as illustrated in FIG. 11 or displaced as illustrated in FIG. 12.

The invention claimed is:

1. Injector device comprising an elongated mixing container extending along a first axis, and a piston member slidably positioned in the mixing container, wherein the injector device further comprises a mixing device comprising a mixing member, an elongated member parallel to the first axis and a handle member, the piston member comprising a piston head having a bore adapted to slidably accommodate the elongated member of the mixing device, wherein the piston member comprises a first locking arm flexibly connected to the piston head, such that the first locking arm in a first position extends substantially parallel to the elongated member and engages with the mixing device in such a way that the piston member moves in a first direction along the first axis with the mixing device, and in a second position allows the mixing device to move relative to the mixing container independently of the piston member.

2. The injector device according to claim 1, wherein the piston member comprises a second locking arm flexibly connected to the piston head, such that the second locking arm in a first position extends substantially parallel to the elongated member and engages with the mixing device in such a way that the piston member moves with the mixing device in a first direction, and in a second position allows the mixing device to move relative to the mixing container independently of the piston member.

3. The injector device according to claim 1, wherein the piston member in the second position engages with the mixing container in such a way, that the piston member is prevented from moving in the first direction in relation to the mixing container.

4. The injector device according to claim 1, wherein the piston member further comprises a first outer seal on the piston head.

5. The injector device according to claim 1, wherein the piston member further comprises a second outer seal on the piston head.

6. The injector device according to claim 5, wherein the piston member comprises a first inner seal in the bore.

7. The injector device according to claim 5, wherein the piston member comprises a second inner seal in the bore.

8. The injector device according to claim 1, wherein the first locking arm in the second position extends parallel to the first axis.

9. The injector device according to claim 1, wherein the first locking arm, in the second position, is bent such that the first locking arm form an angle in the range from 0° to 135° with the first axis in the first direction, where an angle of 0° corresponds to a distal end of the first locking arm pointing in the first direction.

10. The injector device according to claim 1, wherein the first locking arm has a distal end formed to, in the first position, engage with or support on the handle member.

11. The injector device according to claim 1, wherein the piston member comprises a first hinge part formed between the piston head and the first locking arm for flexibly connecting the first locking arm to the piston head.

12. The injector device according to claim 2, wherein the piston member comprises a second hinge part formed between the piston head and the second locking arm for flexibly connecting the second locking arm to the piston head.

13. Method for mixing a first component and a second component using an injector device comprising an elongated mixing container extending along a first axis, and a piston member slidably positioned in the mixing container, wherein the injector device further comprises a mixing device comprising a mixing member, an elongated member parallel to the first axis and a handle member, the piston member comprising a piston head having a bore adapted to slidably accommodate the elongated member of the mixing device, wherein the piston member comprises a first locking arm flexibly connected to the piston head, the method comprising:
   providing a first and a second component in the mixing container,
   bending the first locking arm into a second position, wherein the mixing device is allowed to move relative to the mixing container independently of the piston member,
   mixing the first and second component by moving the mixing device along the first axis,
   moving the first locking arm into a first position, wherein the first locking arm extends substantially parallel to the elongated member and engages with the mixing device in such a way that the piston member is moved in a first direction along the first axis with the mixing device, and
   moving the mixing device in the first direction.

14. The injector device according to claim 2, wherein the piston member in the second position engages with the mixing container in such a way, that the piston member is prevented from moving in the first direction in relation to the mixing container.

15. The injector device according to claim 2, wherein the piston member further comprises a first outer seal on the piston head.

16. The injector device according to claim 2, wherein the piston member further comprises a second outer seal on the piston head.

17. The injector device according to claim 6, wherein the piston member comprises a second inner seal in the bore.

18. The injector device according to claim 2, wherein the first locking arm in the second position extends parallel to the first axis.

19. The injector device according to claim 1, wherein the first locking arm, in the second position, is bent such that the first locking arm form an angle in the range from 0° to 45°, with the first axis in the first direction, where an angle of 0° corresponds to a distal end of the first locking arm pointing in the first direction.

20. The injector device according to claim 2, wherein the first locking arm has a distal end formed to, in the first position, engage with or support on the handle member.

* * * * *